United States Patent [19]

Schulte

[11] Patent Number: 5,432,183

[45] Date of Patent: Jul. 11, 1995

[54] USE OF RAPAMYCIN PRODRUGS AS IMMUNOSUPPRESSANT AGENTS

[75] Inventor: Gary R. Schulte, Stonington, Conn.

[73] Assignee: Pfizer Inc., New York, N.Y.

[21] Appl. No.: 142,422

[22] PCT Filed: Apr. 3, 1992

[86] PCT No.: PCT/US92/02504

§ 371 Date: Nov. 30, 1993

§ 102(e) Date: Nov. 30, 1993

[87] PCT Pub. No.: WO92/21341

PCT Pub. Date: Dec. 10, 1992

Related U.S. Application Data

[63] Continuation-in-part of Ser. No. 708,412, May 31, 1991, abandoned.

[51] Int. Cl.⁶ .................. A61K 31/395; C07D 491/6; C07D 491/16
[52] U.S. Cl. ...................................... 514/291; 540/456
[58] Field of Search .................. 540/436; 514/291

[56] References Cited

U.S. PATENT DOCUMENTS

| 4,650,803 | 3/1987 | Stella et al. | 340/456 |
| 5,200,411 | 4/1993 | Edmunds et al. | 540/456 |

FOREIGN PATENT DOCUMENTS

| 227355 | 7/1987 | European Pat. Off. | 540/456 |
| 401747 | 12/1990 | European Pat. Off. | 540/456 |
| 2244991 | 12/1991 | United Kingdom | 540/456 |
| WO92/21341 | 12/1992 | WIPO | 540/456 |

OTHER PUBLICATIONS

J. Am. Chem. Soc., vol. 91, pp. 1409–1411 (1991) Fretz et al.
Tetrahedron Letters, vol. 33 pp. 2295–2298 (1992) Curran et al.
Canadian J. Physiology and Pharmacology vol. 55 (1977) pp. 48–51.

*Primary Examiner*—Robert T. Bond
*Attorney, Agent, or Firm*—Peter C. Richardson; Paul H. Ginsburg; Grover F. Fuller, Jr.

[57] ABSTRACT

The use of rapamycin prodrugs of formula I as immunosuppressant agents, intermediates formed in the preparation of its prodrugs as well as the prodrugs themselves.

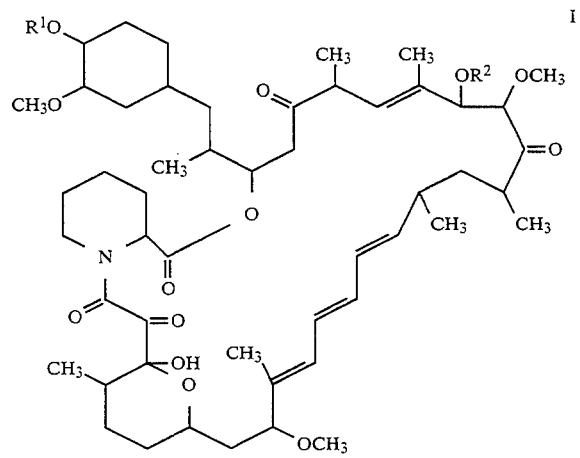

22 Claims, No Drawings

USE OF RAPAMYCIN PRODRUGS AS IMMUNOSUPPRESSANT AGENTS

This application is a 371 of PCT/U.S. 92/02504 filed 3 Apr. 1992 and a C-I-P of Ser. No. 07/708,412, filed 31 May 1991, now abandoned.

BACKGROUND OF THE INVENTION

This invention relates to the use of rapamycin prodrugs as immunosuppressant agents, e.g. for use in a human host in the treatment of autoimmune diseases and/or prevention of organ transplant rejections, intermediates formed in the preparation of the prodrugs as well as the prodrugs themselves.

In 1983, the United States Food and Drug Administration licensed cyclosporin A, an anti-rejection drug that revolutionized the field of organ transplant surgery. The drug acts by inhibiting the body's immune system from mobilizing its vast arsenal of natural protecting agents to reject the transplant's foreign protein. Although cyclosporin A is effective in fighting transplantation rejection, it suffers drawbacks in causing kidney failure, liver damage, and ulcers which in many cases can be very severe. Newer, safer drugs exhibiting less side effects are constantly being searched for.

Rapamycin has been found to be useful as an antifungal agent, U.S. Pat. No. 3,929,992, as well as capable of inhibition of the immune response, Martel, et al., Can. J, Physiol. Pharmacol., 55, 48–51 (1977).

SUMMARY OF THE INVENTION

The present invention relates to a method for suppressing the immune system, for example, in treating autoimmune disease or preventing or ameliorating organ or tissue transplant rejection comprising administering to a mammal in need of such treatment an effective immunosuppressive amount of a compound of the formula

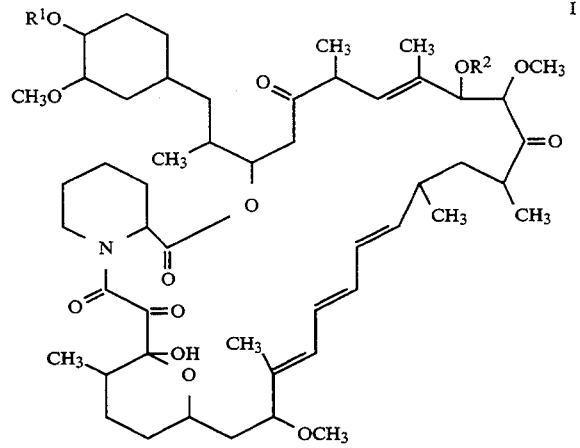

I wherein $R^1$ and $R^2$ are independently selected from hydrogen, and a group of the formula

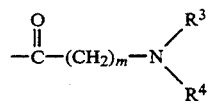

II wherein m is 1–6, $R^3$ and $R^4$ are each hydrogen; branch or straight $C_1$ to $C_8$ alkyl; cyclic $C_3$ to $C_4$ alkyl; phenyl; benzyl; or $R^3$ and $R^4$ taken together with the nitrogen to which they are attached form a saturated heterocyclic ring having four or five carbon atoms, with the proviso that $R^1$ and $R^2$ can not both be hydrogen. In a preferred embodiment of the present invention, at least one of $R^1$ and $R^2$ is a group of the formula II more, even preferred, $R_3$ and $R_4$ are $C_1$ to $C_8$ alkyl.

The present invention also relates to intermediates for forming prodrugs of rapamycin of formula I wherein $R_1$ or $R_2$ are each independently

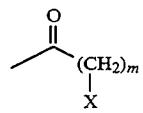

III

X is a suitable leaving group, and m is 1 to 6. Preferred leaving groups include, Br, Cl, I, $-OSO_2CH_3$, and p-toluenesulfonate.

The present invention also relates to prodrugs of rapamycin of formula I wherein $R^2$ is hydrogen and $R^1$ is

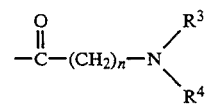

IV wherein n is 1 to 6; $R^3$ and $R^4$ are each independently hydrogen; branch or straight $C_1$ to $C_8$ alkyl; cyclic $C_3$ to $C_8$ alkyl; phenyl; benzyl; or $R^3$ and $R^4$ taken together with the nitrogen to which they are attached to form a saturated heterocyclic ring having four or five carbons atoms, or pharmaceutically acceptable salts thereof, as well as pharmaceutical compositions including the prodrugs.

DETAILED DESCRIPTION OF THE INVENTION

The compounds of formula I are rapamycin prodrugs. Rapamycin and certain prodrugs thereof are described in U.S. Pat. Nos. 3,929,992; 3,993,749; 4,316,885; and 4,650,803, the disclosure of which is hereby incorporated herein by reference.

The prodrug compounds of the present invention are produced by first forming the alkanoate ester of rapamycin. This is accomplished by reacting rapamycin, the compound of formula I where $R_1$ and $R_2$ are both hydrogen, with an acylating agent of the formula $YCO(CH_2)_mX$ (V) where m is as defined above, in the presence of an alkylamine base and a non-polar solvent. For the acylating agent of formula V, Y is, for example, halogen, $N_3$, $-O-COCH_2-X$,

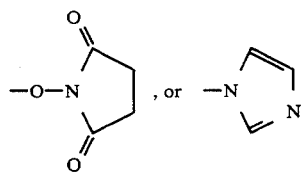

and X is a suitable leaving group such as, for example, halogen,

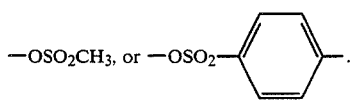

Preferably the acylating agent is where X and Y are each a bromine atom. Suitable amine bases include the following bases:

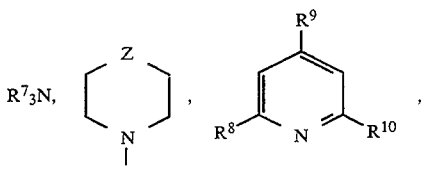

wherein
$R^7 = C_1$ to $C_4$ alkyl, $C_5$–$C_6$ cycloalkyl
$Z = -(CH_2)_m-$, $-O-$;
$m = 0, 1$
$R^9 = H$, $C_1$ to $C_4$ alkyl, $N(CH_3)_2$;
$R_8$, $R_{10} = H$, $C_1$ to $C_4$ alkyl;
$n = H, 1, 3$.

Mono- and dialkylamine bases will react with the acylating substrate and alkali hydroxides and alkali hydrides will cause reaction to the macrolide substrate. Preferably a trialkylamine base is used; the preferred is 2,4,6-collidine. Single or mixtures of the following solvents can be used: (1) hydrocarbons (i.e., pentane, hexane, and cyclohexane), (2) halocarbons (i.e., methylene chloride, chloroform, dichloroethane, and carbon tetrachloride), (3) aromatic hydrocarbons (i.e., benzene or toluene), and (4) ethers (i.e., diethyl ether, tetrahydrofuran, dimethoxyethane, and dioxane); preferably, dichloromethane is used. Reaction conditions range from about −78° C. to about +50° C. in temperature; preferably about −43° C. is used Reactions are carried out under an inert atmosphere using, for example, nitrogen or argon gas. Reaction times typically range from 5 minutes to 24 hours, preferably about 5 hours.

After the first step, the reaction mixture includes rapamycin substituted at the 28 position, the 43 position, and both positions. Standard flash chromatography, which separates based on polarity, is used to isolate each of the three substituted rapamycins in order to proceed with each separately.

The second step involves reacting the acetate ester of rapamycin with a nucleophile of the formula $HNR_3R_4$ to form the corresponding glycinate ester. For the nucleophile, $R_3$ and $R_4$ are each independently hydrogen; branch or straight $C_1$ to $C_8$ alkyl; cyclic $C_3$ to $C_8$ alkyl; phenyl; or benzyl; preferably each is methyl. For nonpolar solvent choices the following are used in mixtures or independently and include the previously described (1) halocarbons, (2) aromatic hydrocarbons, and (3) ethers as well as (4) polar aprotic solvents (i.e., N,N-dimethylformamide, dimethylsulfoxide, and acetonitrile), preferably dimethylformamide is used. The reaction is run in a range of temperatures from about −78° C. to approximately room temperature (about 27° C.); preferably about −45° C. is used. The reaction is run under an inert atmosphere of, for example, nitrogen or argon.

The prodrug salts of the glycinate ester are formed by reacting the amine of the ester with mineral and organic acids ($H^+ - X$) where X is, for example halogen, $HSO_4$, $H_2PO_4$, $HCO_3$, $R^7COO$, and $R^7SO_3$ where $R^7$ is $C_1$–$C_{24}$ alkyl, $C_1$–$C_{24}$ alkenyl, or phenyl. Preferably X=Cl, $MeSO_3$, MeCOO, or $CH_3(CH_2)_7CH=CH(CH_2)_7COO$ (oleate). The solvents for salt formation are: (1) hydrocarbons, (2) halocarbons, (3) aromatic hydrocarbons, and (4) ethers, described above; preferably diethyl ether is used. All salt formations are carried out at temperatures ranging from −78° C. to room temperature; preferably 0° C. is used.

Rapamycin and its prodrugs exhibit immunosuppressive activity, i.e., positive inhibition of T-cell activation. The immunosuppressant effect of rapamycin and its prodrugs may be demonstrated by the following assays. Immunosuppression can be measured by measuring $3H$-thyroidins uptake in human lymphocytes. The procedure is a modified two-way mixed lymphocyte reaction using frozen donor cells as a stimulator population and freshly isolated cells as a responder population.

The responder population is prepared by drawing human blood into a sterile syringe containing 0.8 ml (preservative free heparin (1,000 USP units/mi.)). Twenty-five ml of the blood and 20 ml of RPMI-1640 lymphocyte medium are added and mixed in a centrifuge tube. The mixture is then underlayed with 10 ml HISTOPAQUE-1083 (SIGMA) and centrifuged at room temperature for about 30 minutes at approximately 925 g. After centrifugation is complete, the mononuclear cells in the layer of HISTOPAQUE-1083, the third layer from the top, are drawn off. These cells are then reconstituted with RPMI-1640, centrifuged for 5 minutes at 1800 rpms, supernatant removed, and resuspended in RPMI-1640. This washing procedure is repeated twice more. After the final washing, the medium in which cells are suspended (RPMI-1640) is enriched with 0.5% MEM non-essential amino acids (100x) solution, 1% L-glutamine (200 mM), 1% MEM vitamins (100x), 1% penicillin streptomycin solution (10,000 Units/ml), and 15% heat-inactivated human AB serum (NABI). The cells are adjusted in concentration to about $5 \times 10^5$/ml and 100 μl/well of cell stock added to round bottom 96 well plates.

The stimulator pool is prepared by collecting blood from seven different donors blood, separating, and washing mononuclear cells as described above with the responder population up to and including the washing steps. After the final wash, the mononuclear cells from the donors are pooled and suspended at $2 \times 10^7$ cells/ml in 90% human AB serum and 10% DMSO and stored in liquid nitrogen. When ready to perform the assay, the frozen cells are placed in a water bath at a temperature of about 37° C. until thawing begins. The cells are removed from the bath at that point and room temperature RPMI-1640 is added to the pellet. After the cells have thawed completely, they are washed once in RPMI- 1640, resuspended in a minimum volume, and viability is determined using, e.g., trypan blue exclusion stain (viability should be in excess of 80%). Those cells meeting the viability standard are diluted with RPMI-1640 to a concentration of $5 \times 10^5$ cells/ml and 100μl/well of stimulator cells are added to the wells containing the responder cells.

The test compounds are solubilized in either ethanol or DMSO (10%) and sterile water (90%). The concentrations of the solubilized compounds is adjusted such that the addition of 50 μl of test compound solution will result in final concentrations in each well of 10, 1, or 0.1 mg/ml. The assay for each dose is run in triplicate wells and the plates are incubated at about 37° C. in 5% $CO_2$, humidified for 5 days. One μCi/well of $^3$H-thymidine is then added to each well and the plates are incubated for another 18 hours, after which the cells are harvested and tritium counted using the LKB BETA PLATE counter system.

Controls for the assay included triplicate well of responder and stimulatory cells run separately (unstimulated) as well as the above referred to 1:1 mixture of those cells without the addition of drug (stimulated). The uptake of $^3$H-thymidine for each of the wells is determined and the average cpm value for each set of triplicates is calculated. The % inhibition is calculated using the following formula:

inhibition = [1-(avg. cpm with drug)/(avg. cpm stimulated control)]X 100.

Inhibition of 50% or better at any compound concentration is considered active.

A second assay involves. evaluating interleukin-2 biosynthesis inhibition. A rat spleen cell suspension is first prepared by sacrificing rats. The spleens from the rats are minced and gently pushed through a fine meshed screen with frequent washings with RPMI-1640, 5% heat-inactivated fetal calf serum (FCS), 100 μg streptomycin/ml, and 2 mM 1-glutamine (RPMI/5). Approximately $5 \times 10^8$ spleen cells are recovered from each 200-250 g rat. The rat spleen cells are resuspended in RPMI/5 at a concentration of $5 \times 10^6$ cells/ml. 2 μg/ml of Con A is added to the cell suspension.

CTLL-2 cells are also prepared using known methods and are maintained prior to the assay in 60%RPMI 1640, 10% FCS, pen/strep, 1-glutamine (RPMI/10) with 40% rat growth factor. Rat growth factor is a mixture of cytokines prepared by incubating $5 \times 10^6$ rat spleen cells/ml with 2 μg/ml Con A for 48 hours in RPMI/5. Cultures are then centrifuged and the supernatants sterile filtered and stored at −20° C. until used.

Approximately i mg of a test compound is dissolved in 1.0 ml of approximately 10% DMSO or ethanol and 90% phosphate buffered saline (PBS) or sterile water. Compounds are then further diluted in RPMI/5 to a final concentration of 30.0, 3.0, and 0.3 μg/ml. 0.1 ml of each concentration of test compound is added in triplicate to each well of a tissue culture plate which already contains 0.1 ml of the above spleen cell suspension. 0.1 ml of media is also added to each well, giving a final test compound concentration of 10.0, 1.0, and 0.1 μg/ml. The cells are incubated with humidification under 5% $CO_2$ at 37° C. for about 24 hours. After the incubation, 0.1 ml of supernatant is removed and added to the wells of another tissue culture plate containing the CTLL-2 cells. The spleen cells are saved for viability determinations.

The day before the CTLL-2 cells are used, they are washed and resuspended in RPMI/10 without rat growth factor at $10^5$ cells/ml, and 0.1 ml plated into the wells of a 96 well tissue culture plate to which 0.1 ml of the above spleen cell suspension has already been added. After addition of test supernatant, the plates are incubated for 48 hours with humidification under 5% $CO_2$ at 37° C. Six hours before harvesting, 1.0 μCi tritiated thymidine (spec. act. 2.0 Ci/mM) is added to each well. The cells are then harvested and tritium counted (using the LKB BETA PLATE system).

Percent inhibition is calculated relative to introduction of only Con A as control supernatant and is determined for each concentration. Viability of the spleen cells and the CTLL-2 cells is also assessed. Compounds which inhibit IL-2 production 80% or more, which do not decrease viability of the spleen cells more than 80% compared to Con A controls, and which are not toxic to the CTLL-2 cells are considered active.

A third assay for delayed-type hypersensitivity (DTH) can be used to determine the ability of compounds to inhibit the delayed response of sensitized mice to a challenge of sheep red blood cells. The assay uses 20 g $C_{57}BL/6$ male mice (Charles River Breeding Laboratories), typically five per group. Defibrinated sheep blood can be purchased from, for example, Scott Laboratories, Inc. On the first day sheep red blood cells are prepared by centrifuging about 4 ml of sheep red blood cells (srbcs) for 10 min. at 3000 rpms. The supernatant is poured off and the red cells are resuspended in 9 mls of sterile saline. This washing step is performed twice more. The red blood cells are then adjusted to a concentration of $5 \times 10^6$/ml.

Animals are treated with 0.2 ml of a test compound in 10% ETOH, DMSO, or similar vehicle. Control groups include a vehicle control, and non-treated immune control, and a normal, i.e., non-sensitized, group. Also, on the first day and approximately 1 hour after the above treatment (depending on which group a given animal is in), animals are sensitized by injecting $10^6$ srbcs in 0.2 ml i.v. Animals are treated daily for four additional days. On day 4, srbcs are prepared as before, except that the final concentration is adjusted to $3 \times 10^8$/ml. Approximately 1 hour after treatment, animals are challenged by implanting $10^8$ srbcs into the planar surface of 1 hind footpad in a volume of 0.03 ml.

Approximately 24 hours after challenge, the thickness of both hind footpads is measured with dial gauge calipers. The increase in footpad size of the challenged footpad versus the control footpad is a measure of DTH, and is typically in the range of 0.8 to 1.2 mm.

Results are reported as % inhibition on DTH in drug treated groups versus control.

Rapamycin prodrugs of the present application possess immunosuppressive activity and antimicrobial activity, and are therefore useful for the treatment, prevention of the rejection of transplanted organs and tissues (such as heart, heart-lung, kidney, liver, medulla ossium, skin, etc.), autoimmune diseases such as rheumatoid arthritis, systematic lupus erythematosus, Hashimoto's thyroidiris, multiple sclerosis, myasthenia gravis, type I diabetes, uveitis, obstructive airway diseases, and psoriasis), as well as infectious diseases caused by pathogenic microorganisms.

The pharmaceutical compositions of the present invention can be used in the form of a pharmaceutical preparation, for example, in solid, semi-solid or liquid form, which contains the rapamycin prodrugs as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspension, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations., in solid, semi-solid, or liquid form, and in addition auxiliary, stabilizing, thickening and coloring agents and perfumes may be used.

For applying such pharmaceutical compositions to a human, it is preferable to apply the compositions by parenteral or oral administration. While the dosage of therapeutically effective amount of the rapamycin prodrug depend upon the age and condition of each individual patient to be treated, a daily dose of from about 1 mg/kg to about 250 mg/kg preferably about 20 mg/kg and an average single dose of about 0.5 mg, 1 mg, 5 mg, 10 mg, 50 mg, 100 mg, 250 mg is generally administered.

The following example are given for the purpose of illustrating the present invention and should not be construed as being a limitation on the scope of the instant invention.

EXAMPLE 1

43-bromoacetate ester of rapamycin

Rapamycin (5.0 gm, 5.47 mmol) was dissolved in 500 ml of dichloromethane and then the solution was cooled to −72° C. (acetone/dry ice bath). 2, 4, 6 - Collidine (14.46 ml, 109.41 mmol) and bromoacetylchloride (4.06 ml, 49.23 mmol) were sequentially added to the cold rapamycin solution. After 4.5 hours additional 2, 4, 6 - Collidine (7.12 ml, 53.86 mmol) and bromoacetylchloride (2.00 ml, 24.24 mmol) were added. The reaction was worked up by pouring into a 5% sodium bicarbonate/ice (400 ml/600 ml) mixture after 5.5 hours total reaction time. The aqueous solution was extracted with ethyl acetate (800 ml). The organic solution was washed with 5% sodium bicarbonate (4×500 ml) followed by 1n hydrochloric acid (4×500 ml), dried (anhydrous sodium sulfate) and filtered. Evaporation followed by chromatography (SiO$_2$; hexanes/ethyl acetate, 1:1) gave pure title compound (2.0 g, 1.94 mmol, 35% yield) as a glass.

Physical data: Fast atom bombardment mass spec.: m/z 1057/1059 ((M+Na) +5%) 1034/1036 ((M+H)$^+$, 10%); partial $^1$H NMR (CH$_2$Cl$_2$): δ 4.68 (1H, ddd) and 3.85 (2H, brs).

EXAMPLE 2

43-N,N-dimethylglycinate ester of rapamycin

A sample of 43-bromoacetate ester of rapamycin (1.01 g, 0.978 mmol) was dissolved in 20 ml of N,N-dimethylformamide and then cooled to −45° C. (acetonitrile/dry ice). To this solution excess dimethylamine (1 ml) in 3 ml of N,N-dimethylformamide was slowly added by addition funnel so as to maintain the reaction solution below −40° C. After 1 hour the reaction was complete and poured into 600 ml of brine and ice. The aqueous solution was extracted with ethyl acetate (2×250 ml). The ethyl acetate solution was washed with brine (3×100 ml), dried (Na$_2$SO$_4$), filtered and evaporated to give pure title compound (0.95 g, 0.957 mmol, 98% yield) as a glassy solid.

Physical data: Fast atom bombardment mass spec.: m/z 1021 ((M+Na)$^+$, 5%), 999 ((M+H)$^+$, 100%); partial $^1$H NMR (CD$_2$Cl$_2$): δ 4.68 (1H, ddd), 3.12 (2H, brs), and 2.30 (6H, brs).

EXAMPLE 3

Methanesulfonic acid salt of 43-N,N-dimethylalycinate ester of rapamycin

A sample of 43-N,N-dimethylglycinate ester of rapamycin (0.95 g, 0.952 mmol) was dissolved in 5 mL of dichloromethane and cooled to 0° C. A stock solution of methanesulfonic acid (3.25 ml, 49.9 mmol) in 46.7 ml of diethyl ether was prepared. A 1 ml aliquot of the acid solution was slowly added to the cooled aminoester. After addition the solution was evaporated to give the title compound (1.02 g, 0.986 mmol, 98% yield) as a light yellow solid, m.p. 100°–120° C.

Physical data: partial $^1$H NMR (CD$_2$Cl$_2$): δ 11.59 (1H, exchangeable), 4.79 (1H, ddd), 3.88 (2H, brs), 3.00 (6H, brs), and 2.73 (3H, s).

I claim:

1. A method for suppressing the immune system comprising administering to a mammal in need of such treatment an effective immunosuppressive amount of a compound of the formula

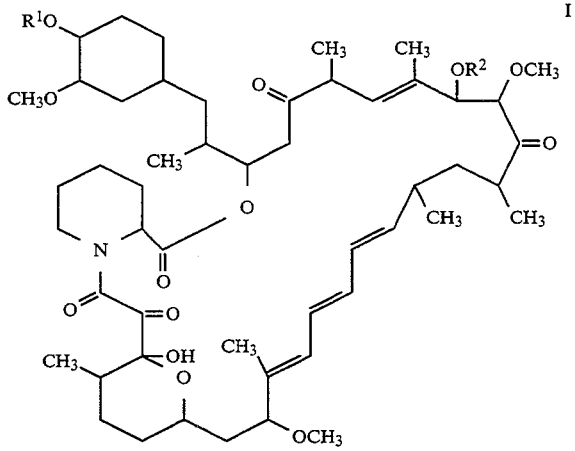

wherein R$^1$ and R$^2$ are independently selected from hydrogen, and a group of the formula

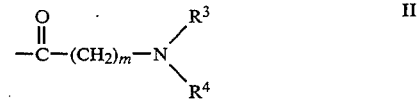

wherein m is 1–6, R$^3$ and R$^4$ are each independently hydrogen; branch or straight C$_1$ to C$_8$ alkyl; cyclic C$_3$ to C$_8$ alkyl; phenyl; benzyl; or R$^3$ and R$^4$ taken together with the nitrogen to which they are attached form a saturated heterocyclic ring having four or five carbon atoms, with the proviso that R$^1$ and R$^2$ cannot both be hydrogen.

2. The method of claim 1, wherein said method is used in treating autoimmune disease.

3. The method of claim 1, wherein said method is used in preventing or ameliorating organ or tissue transplant rejection.

4. The method according to claim 1, wherein R$^3$ and R$^4$ are each independently a straight C$_1$ to C$_8$ alkyl chain.

5. The method according to claim 4, wherein R$^3$ and R$_4$ are both methyl.

6. The method according to claim i wherein m is 1.

7. The method according to claim i wherein R$^1$ is

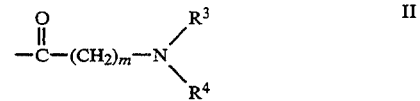

wherein m is 1-6, $R^3$ and $R^4$ are each independently hydrogen; branch or straight $C_1$ to $C_8$ alkyl; cyclic $C_3$ to $C_8$ alkyl; phenyl; benzyl; or $R_3$ and $R_4$ taken together with the nitrogen to which they are attached form a saturated heterocyclic ring having four or five carbon atoms.

8. The method according to claim 7, wherein $R^3$ and $R^4$ are each independently a straight $C_1$ to $C_8$ alkyl chain.

9. The method according to claim S wherein $R^3$ and $R^4$ are both methyl.

10. A compound of the formula

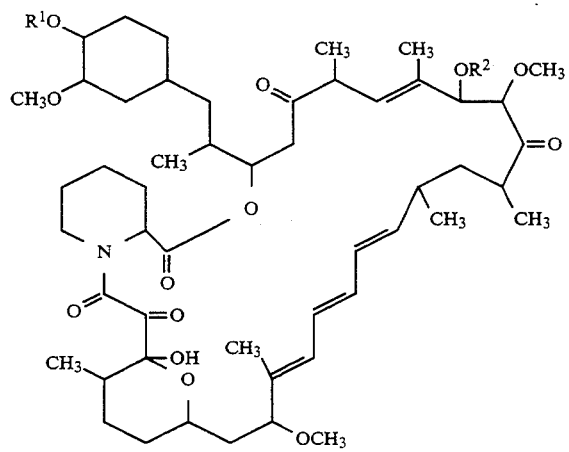

wherein $R_1$ or $R_2$ are each independently

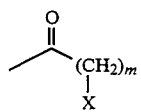

X is a suitable leaving group, and m is i to 6.

11. The compound of claim 10, wherein X is Br, Cl, or I.

12. The compound of claim 11, wherein X is Br.

13. The compound of claim 10, wherein m is 1.

14. The compound of claim 10, wherein the leaving groups are Br, —$OSO_2CH_3$ or p-toluenesulfonate.

15. The compound of claim 10, wherein $R^1$ is

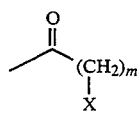

X is a suitable leaving group, and m is 1 to 6.

16. The compound of claim 15, wherein the leaving groups are Br, —$OSO_2CH_3$ or p-toluenesulfonate.

17. The compound of claim 16, wherein the leaving group is a bromine group.

18. A compound of the formula

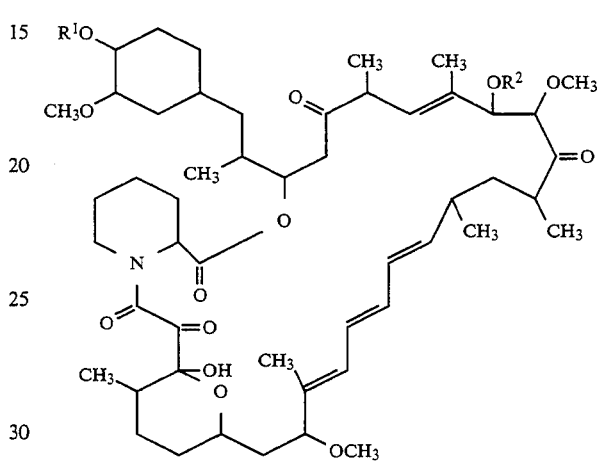

wherein $R^2$ is hydrogen and $R^1$ is

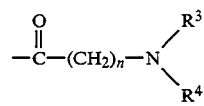

wherein n is 1 to 6; $R^3$ and $R^4$ are each independently hydrogen, branch or straight $C_1$ to $C_8$ alkyl; cyclic $C_3$ to $C_8$ alkyl; phenyl; benzyl; $R^3$ and $R^4$ taken together with the nitrogen to which they are attached to form a saturated heterocyclic ring having four or five carbons atoms, or pharmaceutically acceptable salts thereof.

19. The compound of claim 18, wherein n is 1.

20. The compound of claim 18, wherein $R^3$ and $R^4$ are each independently a straight $C_1$ to $C_8$ alkyl chain.

21. The compound of claim 18 wherein $R^3$ and $R^4$ are both methyl.

22. A pharmaceutical composition for use in suppressing the immune system comprising an effective immunosuppressive amount of the compound of claim 21 and a pharmaceutically acceptable carrier or diluent.

* * * * *